US006617043B2

(12) United States Patent
Shoher et al.

(10) Patent No.: US 6,617,043 B2
(45) Date of Patent: Sep. 9, 2003

(54) DENTAL BONDING MATERIAL AND METHOD FOR BONDING A POLYMERIC VENEERING MATERIAL OR CERAMIC TO A METAL COPING IN FORMING A DENTAL RESTORATION OR PROSTHESIS

(76) Inventors: Itzhak Shoher, 50 Shlomo Hamelech St., Tel Aviv (IL); Aharon E Whiteman, J.L. Peretz Street 13, Petach Tikvah (IL)

( * ) Notice: Subject to any disclaimer, the term of this patent is extended or adjusted under 35 U.S.C. 154(b) by 0 days.

(21) Appl. No.: 09/993,269

(22) Filed: Nov. 26, 2001

(65) Prior Publication Data

US 2003/0097906 A1 May 29, 2003

(51) Int. Cl.$^7$ .................. A61C 13/083; A61C 13/087; A61C 13/09
(52) U.S. Cl. ........................................ 428/553; 264/19
(58) Field of Search ............................ 419/5; 428/553; 264/19

(56) References Cited

U.S. PATENT DOCUMENTS 4,064,311 A * 12/1977 McLean et al. ............. 428/434
4,742,861 A * 5/1988 Shoher et al. ................ 164/80
4,814,008 A * 3/1989 Shoher et al. ................ 75/252

* cited by examiner

Primary Examiner—Daniel J. Jenkins

(57) ABSTRACT

The dental bonding material of the present invention comprises a composition of precious metal particles consisting essentially of high fusing temperature metal particles having a melting temperature above at least about 1200° C. in a size range between 1 micron and 150 microns and low fusing temperature metal particles having a melting temperature below about 1080° C. with or without a suitable carrier for coating or brushing the dental bonding material upon the surface of a metal framework or coping. The dental bonding material may further include a conventional flux preferably containing the element boron in a concentration of between 0 and 5% by weight of the dental material. It is essential to heat treat the bonding-material after it is coated on the metal surface at a temperature below the melting temperature of the high fusing temperature metal particles and high enough to cause a partial melting of the low fusing temperature metal particles but not a complete melting thereof.

7 Claims, No Drawings

DENTAL BONDING MATERIAL AND METHOD FOR BONDING A POLYMERIC VENEERING MATERIAL OR CERAMIC TO A METAL COPING IN FORMING A DENTAL RESTORATION OR PROSTHESIS

FIELD OF THE INVENTION

The present invention relates to a bonding material for bonding a polymeric veneering material or ceramic to the metal framework or understructure of a dental restoration or prosthesis.

BACKGROUND OF THE INVENTION

In a metal based aesthetic dental restoration such as a dental crown and/or a bridge, a metal framework forms the understructure of the restoration, over which is applied a polymer based veneering material or a ceramic porcelain. The veneering material or ceramic is connected to the underlying metal framework to form the superstructure of the prosthesis or dental restoration. The metal framework can represent the metal overlay or metal underlay in a dental restoration or a metal coping in a crown or bridge.

To enhance the bond strength between the veneering material and the metal framework or coping it is conventional practice to first apply a bonder to the surface of the metal framework before coating the surface with the veneering material or porcelain. Commercially available bonders form a mechanical or chemical bond between the bonder and the metal framework. For polymer based veneering materials such as, for example, acrylics or resins which are applied as a coating over the metal framework the retention between the veneering material and the metal framework is relatively weak and the bond strength between the veneering material and the metal framework is poor.

The bonding material of the present invention forms a fused autogenous bond at the interface between the bonding material and the metal surface and forms an interlock of high mechanical retention to the veneering material resulting in a bond between the veneering material and metal framework or coping which is essentially unbreakable.

SUMMARY OF THE INVENTION

The dental bonding material of the present invention comprises a composition of precious metal particles consisting essentially of high fusing temperature metal particles of irregular geometry having a melting temperature above at least about 1200° C. in a size range between 1 micron and 150 microns and low fusing temperature metal particles having a melting temperature below about 1080° C. with or without a suitable carrier for coating or brushing the dental bonding material upon the surface of a metal coping. The dental bonding material may further include a flux of conventional composition preferably containing the element boron. The concentration of the flux should be in the range of between 0 and 5% by weight of the dental material.

The method of bonding a polymeric veneering material to a metal surface of a metal framework or coping in forming a dental restoration or prosthesis according to the present invention comprises forming a dental bonding material comprising a composition of precious metal particles consisting essentially of high fusing temperature metal particles having a melting temperature above at least about 1200° C. in a size range between 1 micron and 150 microns and low fusing temperature metal particles having a melting tem-perature below about 1080° C., coating the metal surface with bonding material and placing the coated metal framework or coping in a furnace heated to a temperature below the melting temperature of the high fusing temperature metal particles but high enough to cause partial melting of the low fusing temperature metal particles although not complete melting. Partial melting causes a phase change in the low temperature fusing metal particles to occur and provided the heat treatment time period is adequate the partially melted low fusing particles will fuse to one another, to the high fusing temperature particles and to the metal surface of the metal framework. If complete melting of the low fusing particles occur the retentive properties of the bonder is diminished. To form a strong bond the high fusing temperature particles, low fusing temperature particles and the metal surface should be essentially oxide free. A flux in the bonder will maintain an oxide free surface.

DETAILED DESCRIPTION OF THE INVENTION

The bonding material of the present invention is a composition comprising precious metal particles predominantly or essentially of high fusing temperature metal particles having a melting temperature at least above 1200° C. in a size range between 1 micron and 150 microns and low fusing temperature metal particles having a melting temperature below about 1080° C. with or without a flux and with or without a suitable binder for coating or brushing the bonding material on the surface of a dental metal coping. High fusing temperature ceramic particles may be added to the bonder but should be limited to not more than 10% by volume of the bonding material composition. The precious metal particle composition may include between ½% to 20% by weight high fusing temperature metal particles with the remainder of low fusing temperature metal particles. The preferred composition includes between 1.5% and 12 wt % high-fusing temperature metal particles with the remainder of low fusing temperature metal particles.

The high fusing temperature metal particles may be composed of a single metal or metal alloy or of different metal alloy compositions, preferably of precious metals such as platinum and/or palladium, in any desired proportion relative to each other, from zero to one hundred percent, with or without other constituents such as gold, silver, copper, magnesium, aluminum, zinc, gallium, indium, and other metals or elements from the third, fourth, or fifth group of elements of the periodic table. Gold may be added to the highfusing temperature metal particles to increase the affinity of the high-fusing temperature metal particles to the low-fusing temperature metal particles and to the surface of the metal coping upon heat treatment. The geometry of the high fusing temperature metal particles and their size is significant to the present invention. An irregular shaped high fusing particle geometry is preferred over a spherical shaped geometry. High fusing metal particles of irregular shape help absorb excess melt from the low fusing temperature metal particles beyond that which is needed to strongly interconnect all of the particles to each other and to the coping metal surface.

The size of the high fusing temperature metal particles is a factor determining the porosity and void volume of the structure of the bonding material after it is heat treated at a temperature sufficient to partially melt the low fusing temperature metal particles. The heat treatment causes the bonding material to form a porous metal body in the form of a mesh. The dental veneering material is coated upon porous metal body formed after the heat treatment. If the size of the high fusing temperature metal particles are too small the pores in the metal mesh are not large enough to permit the applied veneering material to penetrate the interstices of the metal mesh which is necessary to form an unbreakable mechanical interlock. Thus If the size of the high fusing temperature metal particles are too small the mechanical retention of the polymer veneering material to the bonding material will be relatively poor. Alternatively, if the size of the high fusing temperature metal particles are too large the bonding material is too bulky and is undesirable. The preferred size range for the high fusing temperature metal particles is between 1 μm and 150 μm although the optimum size distribution for the high fusing temperature metal particles should have at least 50% of the. particles sized between 20 and 70 microns.

The low-fusing temperature metal particles are composed preferably of gold or a gold alloy, with gold as the major constituent and should be in a size range comparable to the size range for the high fusing temperature metal particles, i.e., 1–150 microns with a preferred size range between 10 and 50 microns. The shape of the low fusing temperature metal particles is not critical and a spherical shape is preferred. A gold based low fusing alloy having a composition of 97% gold 3% silver is preferred. The bonding material may also include a conventional flux preferably selected from the boron group to maintain an oxide free surface on the high and low fusing temperature metal particles and the surface of the metal coping. The concentration of flux should be between zero and 5% by weight of the dental material.

To facilitate applying the bonding material to the surface of a dental metal framework or coping the precious metal composition should be incorporated into a suitable carrier to form a creamy consistency so that the bonding material may be coated or painted on the surface with a brush or spatula. Any conventional vehicle, preferably a volatile liquid, such as ethylene and/or ethyl glycol may be used. Alternatively, an alcohol and a thixotropic agent may be used. The vehicle carrier should preferably vaporize at the heat treatment temperature.

After applying the bonding material to the metal surface, the coated metal structure should be heat treated at a temperature below the melting temperature of the high fusing temperature metal particles and high enough to cause partial melting of the low fusing temperature metal particles but not a complete melting. The preferred heat treatment temperature is between 1020° C. and 1050° C. and more preferably at about 1035° C. The time of heat treatment is not critical provided it is sufficient to cause partial melting of the low fusing temperature metal particles but not complete melting. A time period of about two minutes should be adequate to cause the low fusing temperature metal particles to partially melt and fuse to the high fusing particles and to the metal surface. When the low fusing particles completely melt the high fusing absorption capability may not be sufficient to effectively absorb all the melt and as such the retentive properties of the bonder is greatly diminished.

The surface composition of the metal framework or coping should preferably contain a similarly low fusing temperature metal such as gold or a gold silver alloy and can represent a surface layer on the metal framework or coping. The thickness of the gold silver layer at the metal surface should preferably be only between about 10–40 microns thick.

The veneering resin material or porcelain is then coated upon the heat treated bonder causing the veneering resin material to penetrate into the mesh formed by the metal particles and to mechanically interlock therewith to form a superior unbreakable bond.

What is claimed:

1. A method of forming a bond between a solid metal coping composed substantially of gold and/or having a solid surface layer of a gold composition and a superstructure of a a polymeric veneering or ceramic material comprising the steps of: coating the metal coping with a dental bonding material composition comprising high fusing temperature precious metal particles and low fusing temperature precious metal particles with the content of said high fusing temperature metal particles being between ½% to 20% by weight and with the remainder of said metal particles being low fusing temperature metal particles, heat treating the coated metal coping at a temperature below the melting temperature of the high fusing temperature metal particles and high enough to cause a partial melting of the low fusing temperature metal particles, and coating the heat treated surface with a polymer based veneering material or ceramic to form an essentially unbreakable bond.

2. A method as defined in claim 1 wherein the content of said high fusing temperature metal particles is between 1.5% and 12% by weight.

3. A method as defined in claim 2 wherein the heat treatment step is performed in a furnace.

4. A method as defined in claim 3 wherein the heat treatment occurs for a period of at least about 2 minutes at a temperature between about 1020° C. and 1050° C.

5. A method as defined in claim 4 wherein the heat treatment temperature is about 1035° C.

6. A method as defined in claim 2 wherein the composition at the metal surface is a low fusing temperature metal layer comprising gold.

7. A method as defined in claim 6 wherein the depth of the low fusing temperature layer is between 10–40 microns.

* * * * *